United States Patent [19]

Erpenbach et al.

[11] Patent Number: 5,296,630
[45] Date of Patent: Mar. 22, 1994

[54] PROCESS FOR CONTINUOUSLY PRODUCING AN ANHYDROUS METHYL ACETATE/METHANOL MIXTURE

[75] Inventors: Heinz Erpenbach, Köln; Klaus Günther, Eppstein/Taunus; Gerog Kohl, Hürth, all of Fed. Rep. of Germany

[73] Assignee: Hoechst Aktiengesellschaft, Fed. Rep. of Germany

[21] Appl. No.: 488,276

[22] Filed: Mar. 2, 1990

[30] Foreign Application Priority Data

Mar. 16, 1989 [DE] Fed. Rep. of Germany ....... 3908555

[51] Int. Cl.$^5$ .............................................. C07C 27/00
[52] U.S. Cl. ........................................................ 560/265
[58] Field of Search ............................................. 560/265

[56] References Cited

U.S. PATENT DOCUMENTS

| | | | |
|---|---|---|---|
| 4,046,807 | 9/1977 | Kuckertz | 562/517 X |
| 4,435,595 | 3/1984 | Agreda et al. | 203/28 X |
| 4,481,146 | 11/1944 | Leupold | 560/265 |

FOREIGN PATENT DOCUMENTS 0060717 9/1982 European Pat. Off. .
1196085 6/1970 United Kingdom ................ 560/265

Primary Examiner—José G. Dees
Assistant Examiner—Joseph M. Conrad
Attorney, Agent, or Firm—Connolly & Hutz

[57] ABSTRACT

A process for continuously producing an anhydrous methyl acetate/methanol mixture by esterifying acetic acid and methanol in the presence of an acidic esterification catalyst is indicated, which comprises carrying out the esterification in a distillation column having $n = 20$ to 50 distillation trays, a) the acetic acid being fed together with the catalyst to a distillation tray which is at a distance of 0.5 n to 0.8 n from the still bottom,
b) feeding 50 to 80% by weight of the total methanol to the still bottom and the remaining methanol to a distillation tray which is 2 to 10 trays above the acetic acid feed tray,
c) feeding methanol and acetic acid into the distillation column at a molar ratio of (1.5 to 3):1,
d) setting a reflux ratio of (0.75 to 1.5):1,
e) taking off the anhydrous methyl acetate/methanol mixture at the top of the column and
f) a water/methanol/acetic acid bottom product with the catalyst from the still bottom.

10 Claims, 1 Drawing Sheet

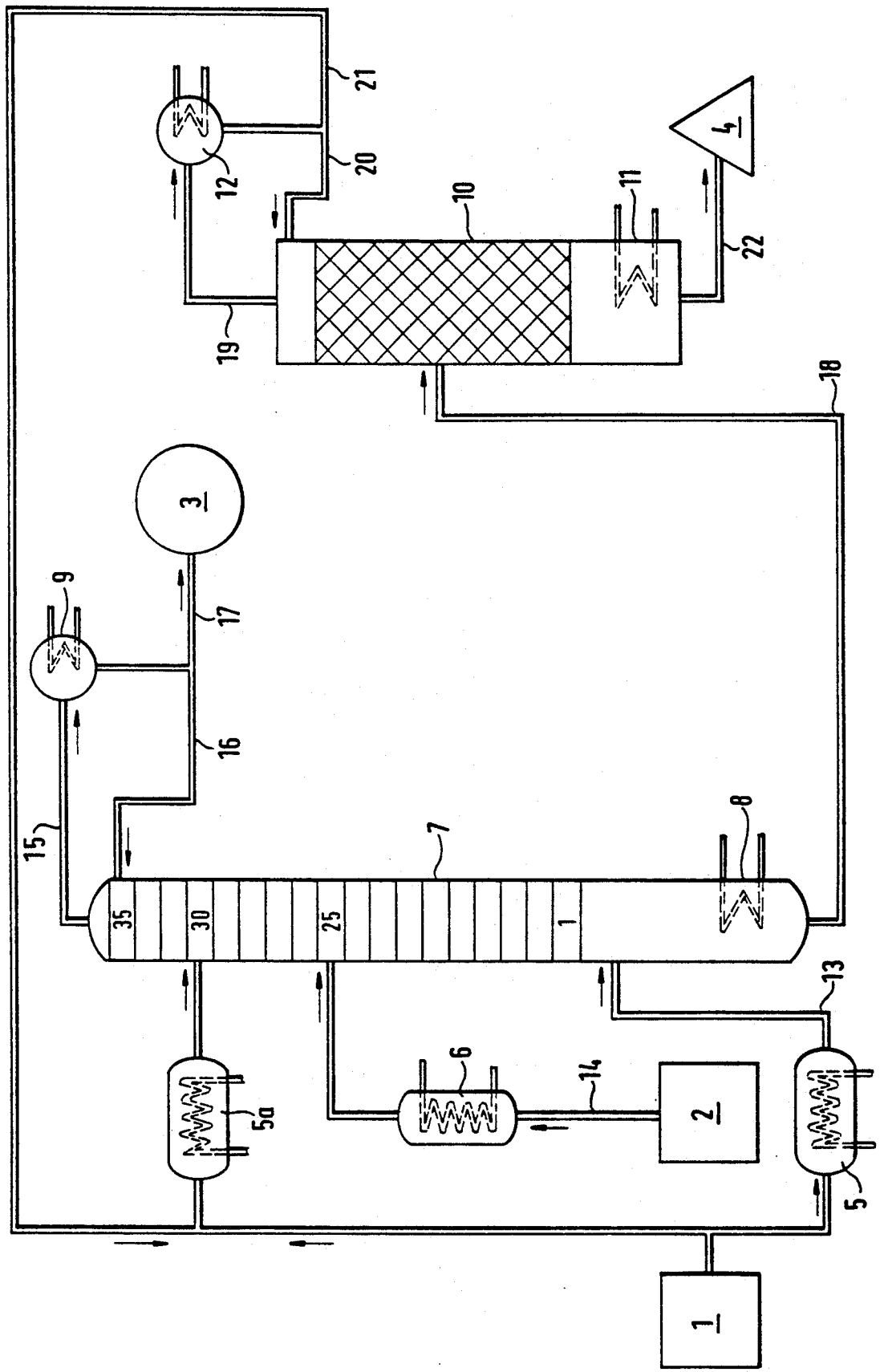

PROCESS FOR CONTINUOUSLY PRODUCING AN ANHYDROUS METHYL ACETATE/METHANOL MIXTURE

The present invention relates to a process for continuously producing an anhydrous methyl acetate/methanol mixture from acetic acid and methanol in the presence of an acidic esterification catalyst.

The esterification of anhydrous acetic acid—also called glacial acetic acid—with methanol in the presence of acidic esterification catalysts such as, for example, sulfuric acid and phosphoric acid or so-called Lewis acids, to give methyl acetate has been part of the state of the art for a long time (see "Ullmanns Encyklopädie der technischen Chemie [Ullmann's Encyclopedia of Industrial Chemistry]", 3rd edition, 1955, volume 6, pages 796 to 797). In order to shift the esterification equilibrium to the side of the ester, the water formed is removed by distillation from the reaction mixture.

In EP-0,060,717 Al, a process for producing methyl acetate by esterification of methanol with acetic acid is described, wherein methyl acetate and water are distilled out of the reaction mixture as an azeotrope by means of an entrainer. This azeotrope can be purified by a further distillation. A methyl acetate is thus obtained which contains 1.5% by weight of methanol, 5.2% by weight of water, 0.002% by weight of acetic acid and 0.05% by weight of n-butyl acetate (entrainer). Without entrainer, a distillate is obtained which also contains, in addition to methyl acetate, 27.9% by weight of methanol, 13.8% by weight of water and 0.8% by weight of acetic acid.

The methyl acetate produced according to EP-0,060,717 Al cannot used in a carbonylation reaction for the production of solely acetic anhydride since, corresponding to the water content, stoichiometric quantities of acetic acid are formed in the carbonylation reaction. The carbonylation reaction for producing acetic anhydride has been previously described in U.S. Pat. No. 4,046,807.

It was therefore the object to indicate a process for continuously producing an anhydrous methyl acetate/methanol mixture, which can be operated at a high yield, relative to acetic acid, at a short residence time in the esterification zone and without an entrainer, and the effluent from which can be purified without problems in a biological treatment plant.

FIG. 1 shows the schematic of the apparatus used to carry out the instant process.

Surprisingly, it was possible to achieve the object by carrying out the esterification in a distillation column having n=20 to 50 distillation trays,
a) the acetic acid being fed together with the catalyst to a distillation tray which is at a distance of 0.5 n to 0.8 n from the still bottom,
b) feeding 50 to 80% by weight of the total methanol to the still bottom and the remaining methanol to a distillation tray which is 2 to 10 trays above the acetic acid feed tray,
c) feeding methanol and acetic acid into the distillation column at a molar ratio of (1.5 to 3):1,
d) setting a reflux ratio of (0.75 to 1.5):1,
e) taking off the anhydrous methyl acetate/methanol mixture at the top of the column and
f) taking off a water/methanol/acetic acid bottom product with the catalyst from the still bottom.

The process according to the invention can also be further developed, if desired, by
1) feeding a methanol/acetic acid mixture having a molar ratio of (1.6 to 2.0):1,
2) setting a reflux ratio of (0.9 to 1.2):1,
3) carrying out the esterification in a distillation column having 30 to 40 sieve trays and adding all the acetic acid to the 20th to 25th sieve tray, introducing 60 to 70% by weight of the total fed methanol in the gaseous state into the still bottom and introducing the remaining methanol 4 to 6 sieve trays above the acetic acid feed,
4) using concentrated sulfuric acid as the esterification catalyst,
5) operating the distillation unpressurized,
6) heating the acetic acid together with the catalyst to a temperature of from 40° to 60° C.,
7) recovering the methanol in a second distillation from the water/methanol bottom product from the still bottom,
8) operating the second distillation at a reflux ratio of (5 to 50):1, especially (10 to 15):1, and
9) recycling the recovered methanol into the esterification stage.

In principle, it is also possible to carry out the esterification according to the invention in distillation columns having more than 50 distillation trays. Because of the increased investment costs, however, the use of more than 50 distillation trays is uneconomical, since the result is merely a slightly increased methyl acetate content in the methyl acetate/methanol mixture. In the case of distillation columns having less than 20 distillation trays, a breakthrough of water into the top product is possible.

Using the process according to the invention, it is now possible to produce a water-free and acid-free (below the usual detection limit of 0.015% by weight of water and 0.005% by weight of acetic acid) methyl acetate/methanol mixture which, according to analysis by gas chromatography, has a total content of foreign components of only about 100 ppm, the foreign components essentially comprising formaldehyde dimethyl acetal, ethyl acetate and methyl formate. In the case of esterification in a distillation column having 35 bubble-cap trays, the anhydrous methyl acetate/methanol mixture contains 20 to 24% by weight of methanol and thus corresponds almost to the composition of the value, given in the literature, for the azeotrope with 18.7% by weight of methanol.

The bottom product in the still bottom contains the methanol, employed in a stoichiometric excess, minus the methanol removed as the top product, as well as 0.5 to 3.0% by weight of acetic acid and the sulfuric acid employed as the catalyst.

The organic constituents can be distilled off in a packed column from the water containing sulfuric acid. Advantageously, this mixture can be recycled as reactant into the first distillation column.

The procedure according to the invention is explained in more detail by reference to the example and the drawing.

EXAMPLE

The distillation column (7) used was a sieve tray column having a diameter of 2.5 m. The column had 35 sieve trays. The tray spacing was 500 mm, and the weir height on each tray was 120 mm. The stripping column

(10) used was a packed column having an internal diameter of 750 mm and a height of 22 m.

7,730 kg/h of acetic acid and 80 kg/h of 98% sulfuric acid from the acetic acid stock (2) were heated in the preheater (6) to 55° C. and fed via line (14) to the 25th sieve tray, relative to the still bottom (8) of the distillation column (7). From the methanol stock (1) and the condenser (12), 2,560 kg/h of methanol were fed via the preheater (5a) at a temperature of 50° C. to the 30th sieve tray. A further 4,500 kg/h of methanol were vaporized in the vaporizer (5) and fed in the gaseous state under control through line (13) to the still bottom (8). The methanol/acetic acid molar ratio was thus 1.71. The still temperature was held at 92.5° C. The top product was passed through the vapor line (15) to the condenser (9). A reflux ratio of 1.1:1 via the reflux line (16) was set. The mean residence time of the products in the column amounted to 0.75 hour. The top temperature of the distillation column (7) was 52° C. 12,200 kg/h of anhydrous methyl acetate/methanol mixture (77.9/22.1% by weight) were taken off via the line (17) into the stock (3). This corresponds to a methyl acetate yield of 99.6%, relative to acetic acid employed.

2,670 kg/h of bottom product from the still bottom (8) were fed under control through the take-off line (18) to the middle of the stripping column (10). The bottom product was composed of 9.0% by weight of methanol, 0.4% by weight of methyl acetate, 1.1% by weight of acetic acid and 3.0% by weight of sulfuric acid, the remainder being water. The top product was fed via the vapor line (19) to the condenser (12) and condensed therein. In the stripping column (10), a reflux ratio of 10:1 via the reflux line (20) was set. The top temperature of the stripping column (10) was 65° C. and the still temperature was 100° C. 250 kg/h of methanol were recycled via line (21) to the distillation column (7). The recycled methanol contained 4.0% by weight of methyl acetate.

2,420 kg/h of effluent from the still (11) were passed via the take-off line (22) to the biological treatment plant (4). The effluent contained 1.24% by weight of acetic acid and 3.3% by weight of sulfuric acid.

We claim:

1. A process for continuously producing an anhydrous methyl acetate/methanol mixture by esterifying acetic acid and methanol in the presence of an acidic esterification catalyst, which comprises carrying out the esterification in a distillation column having n=20 to 50 distillation trays,
   a) the acetic acid being fed together with the catalyst to a distillation tray which is at a distance of 0.5 n to 0.8 n from the still bottom,
   b) feeding 50 to 80% by weight of the total methanol to the still bottom and the remaining methanol to a distillation tray which is 2 to 10 trays above the acetic acid feed tray,
   c) feeding methanol and acetic acid into the distillation column at a molar ratio of (1.5 to 3):1,
   d) setting a reflux ratio of (0.75 to 1.5):1,
   e) taking off the anhydrous methyl acetate/methanol mixture at the top of the column and
   f) taking off a water/methanol/acetic acid bottom product with the catalyst from the still bottom.

2. The process as claimed in claim 1, wherein a methanol/acetic acid mixture having a molar ratio of (1.6 to 2.0):1 is fed.

3. The process as claimed in claim 1, wherein a reflux ratio of (0.9 to 1.2):1 is set.

4. The process as claimed in claim 1, wherein the esterification is carried out in a distillation column having 30 to 40 sieve trays and all the acetic acid is added to the 20th to 25th sieve tray, and wherein 60 to 70% by weight of the total methanol fed are introduced in the gaseous state into the still bottom and the remaining methanol is introduced 4 to 6 sieve trays above the acetic acid feed.

5. The process as claimed in claim 1, wherein concentrated sulfuric acid is used as the esterification catalyst.

6. The process as claimed in claim 1, wherein the distillation is operated unpressurized.

7. The process as claimed in claim 1, wherein the acetic acid is heated together with the catalyst to a temperature of from 40° to 60° C.

8. The process as claimed in claim 1, wherein the methanol is recovered in a second distillation from the water/methanol/acetic acid bottom product from the still bottom.

9. The process as claimed in claim 8, wherein the second distillation is operated at a reflux ratio of (5 to 50):1.

10. The process as claimed in claim 8, wherein the recovered methanol is recycled to the esterification stage.

* * * * *